(12) United States Patent
Mahar et al.

(10) Patent No.: US 9,540,188 B1
(45) Date of Patent: Jan. 10, 2017

(54) PHARMACEUTICAL VIAL PROCESSING SYSTEM AND METHOD

(71) Applicant: Humana Inc., Louisville, KY (US)

(72) Inventors: Michael Mahar, Phoenix, AZ (US); Atin Kapadia, Chandler, AZ (US)

(73) Assignee: Humana Inc., Louisville, KY (US)

( * ) Notice: Subject to any disclaimer, the term of this patent is extended or adjusted under 35 U.S.C. 154(b) by 0 days.

(21) Appl. No.: 15/276,084

(22) Filed: Sep. 26, 2016

Related U.S. Application Data

(63) Continuation of application No. 14/452,955, filed on Aug. 6, 2014, now Pat. No. 9,457,967.

(60) Provisional application No. 61/862,925, filed on Aug. 6, 2013.

(51) Int. Cl.
*G06F 7/00* (2006.01)
*G05B 15/02* (2006.01)
*B65G 51/42* (2006.01)

(52) U.S. Cl.
CPC ............ *B65G 51/42* (2013.01); *G05B 15/02* (2013.01)

(58) Field of Classification Search
None
See application file for complete search history.

(56) References Cited

U.S. PATENT DOCUMENTS

| | | | | |
|---|---|---|---|---|
| 2002/0198624 | A1* | 12/2002 | Greenwald | G06F 19/3462 700/231 |
| 2010/0282003 | A1* | 11/2010 | Hamada | G01N 35/00722 73/863.91 |
| 2011/0076193 | A1* | 3/2011 | Kitagawa | G01N 35/026 422/65 |
| 2014/0212248 | A1* | 7/2014 | Takai | B65G 1/06 414/273 |
| 2015/0298919 | A1* | 10/2015 | Le | B65G 51/24 406/110 |

* cited by examiner

*Primary Examiner* — Yolanda Cumbess
(74) *Attorney, Agent, or Firm* — Standley Law Group LLP

(57) ABSTRACT

An improved pharmaceutical vial processing system and method groups vials on an automated dispensing line according to diverting needs. The improved pharmaceutical vial processing system and method allows vials to travel in close groups. A diversion algorithm determines when gaps between vials are needed to reduce the likelihood that a mechanical diverting device engages the wrong vial to a new location on the dispensing line. The diversion algorithm identifies each vial that needs to be diverted to a target location and employs a "neighbor analysis" to determine whether a gap between neighboring vials is needed before a vial destined for the target station encounters a diverter. Vials that are destined for locations beyond the target station remain grouped. Vials that are behind a vial destined for the target station are held to introduce a gap between the vial destined for the target station and the remaining vials.

16 Claims, 1 Drawing Sheet

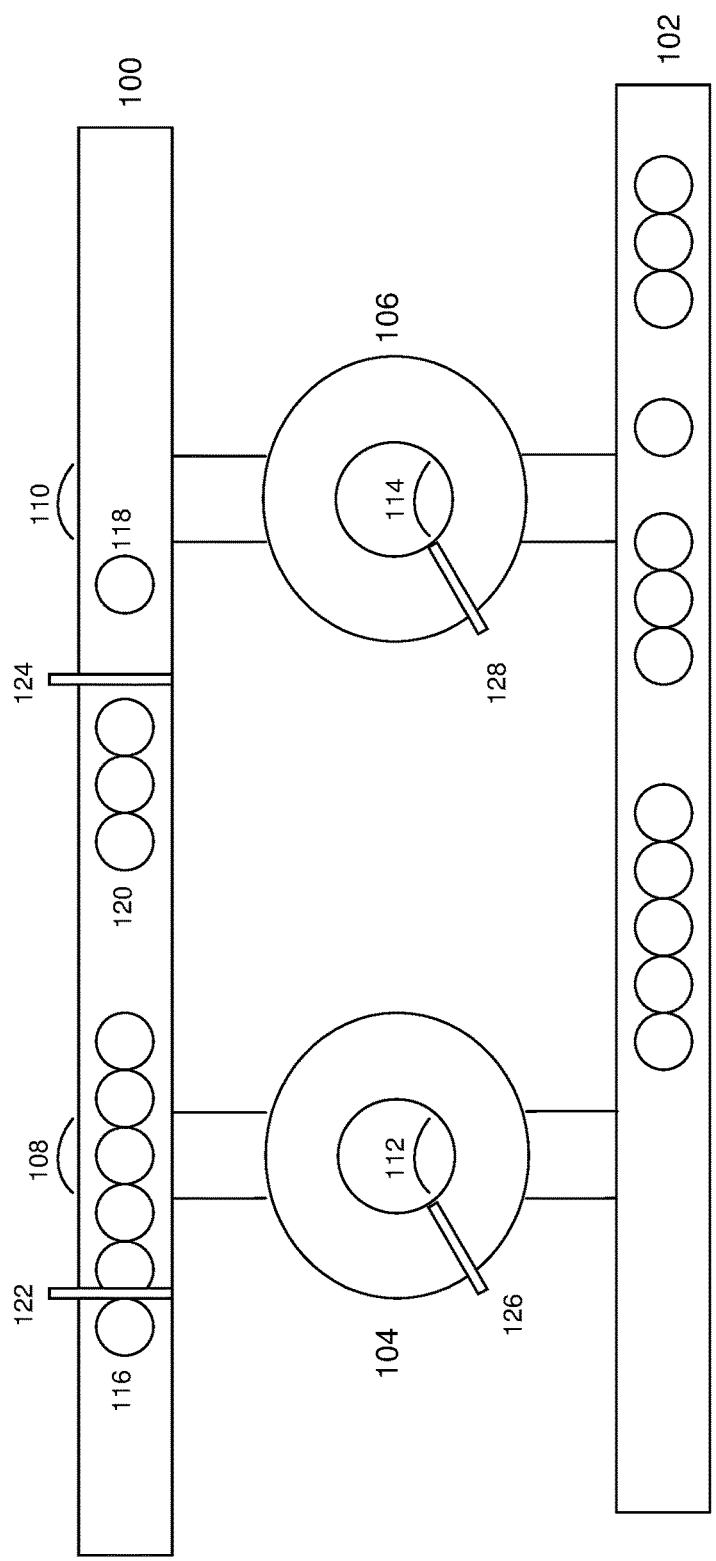

PHARMACEUTICAL VIAL PROCESSING SYSTEM AND METHOD

CROSS-REFERENCE TO RELATED APPLICATIONS

This application is a continuation of U.S. patent application Ser. No. 14/452,955, filed Aug. 6, 2014, issuing Oct. 4, 2016 as U.S. Pat. No. 9,457,967, which claims priority to U.S. Provisional Patent Application No. 61/862,925, titled PHARMACEUTICAL VIAL PROCESSING SYSTEM AND METHOD and filed Aug. 8, 2013, each of which is hereby incorporated by reference in their entirety.

BACKGROUND

Many health benefit plan providers and retail pharmacies offer their clients the option of obtaining prescription drugs by mail. Mail order pharmacies ship prescription drugs to a client's home so the client is not required to visit a pharmacy and to fill a prescription in person. For clients with chronic conditions or other health conditions that require maintenance drugs, a mail order prescription program is an attractive benefit because it is more convenient for the clients and typically less expensive than obtaining prescription drugs at a neighborhood pharmacy. Clients have the option of purchasing many widely-prescribed maintenance drugs in a 60-day or even a 90-day supply at a lower cost than a 30-day supply.

Most mail order pharmacies use automated systems and dispensing lines to process and ship a high volume of prescriptions on a daily basis. Each prescription medication is dispensed into a vial or other container labeled with data from an electronic order that identifies the patient, drug (e.g., by NDC), dosage, and quantity. Each medication is dispensed in its own vial and in many instances, multiple vials are combined into a single package and shipped to a single address for a client with one or more chronic conditions requiring multiple medications. The automated dispensing system, therefore, must be capable of determining which vials should be combined into a single package and routing them accordingly.

One technique for processing multi-prescription orders is to group the vials for the order and process them together so that all vials arrive for packaging and shipping as a group. Although "group processing" of vials is a logical approach to processing and packaging vials destined for a single address, it is not an efficient approach. Implementation of "group processing" on an automated dispensing line may require development of sophisticated algorithms for determining a reasonable or adequate route for the vials to travel as well as holding or reordering of other orders to permit the vials for a multi-prescription order to travel on the line as a group. The requirement for holding and reordering of orders increases vial processing time. In addition, processing of the vials in a group may require longer overall travel times for the vials as the vials are routed as a group and required to make unnecessary stops at stations other than the one station that has the appropriate medication for the vial.

A more efficient approach to processing of multi-prescription orders involves processing each vial of medication separately and then sorting and consolidating or regrouping them for packaging and shipping to a single address. Single vial processing is typically more efficient than group vial processing and reduces the overall travel and processing time for each vial. Single vial processing, however, requires the development of methods for tracking the vials during processing and eventually, sorting and consolidating them for packaging and shipping. The sorting/consolidation process typically involves diverting vials of a multi-prescription order to a sorting station where vials are held until all of the vials for an order have arrived. The vials are grouped at the station and then released for packaging.

Automated dispensing lines typically comprise multiple sorting stations and therefore, require functionality to route and divert vials to the appropriate station. The process of routing and diverting vials for sorting and consolidation as well as other reasons can increase vial travel and processing time. One cause for increased processing times is the need for gaps between vials on the line. On automated dispensing lines, vials are diverted or pushed off a conveyor to a station (or off a station to a conveyor) using a mechanical diverting device that engages when a vial that needs to be diverted or routed to a new location passes in front. To reduce the likelihood that the wrong vial is diverted or that the vials in front of or behind the vial to be pushed are not engaged by the diverter device, all vials on the line are singulated and a distance of at least several millimeters is maintained between vials at some points, or possibly all points, on the line. The process of introducing and/or maintaining gaps between vials increases travel and processing time as one or more vials may be held at various points during processing to ensure a gap is maintained.

Processing times for vials on an automated dispensing line are impacted by various routing and diverting techniques that are employed to facilitate single vial processing as well as multi-prescription order processing. There is a need for an improved pharmaceutical vial processing system and method that reduces processing delays attributable to routing and diverting techniques.

SUMMARY

The present disclosure describes an improved pharmaceutical vial processing system and method that groups vials on an automated dispensing line according to diverting needs. The improved pharmaceutical vial processing system and method allows vials to travel in close groups. A diversion algorithm determines when gaps between vials are needed to reduce the likelihood that a mechanical diverting device engages the wrong vial to a new location on the dispensing line. The diversion algorithm identifies each vial that needs to be diverted to a target location or station and employs a "neighbor analysis" to determine whether a gap between neighboring vials is needed before a vial destined for the target location or station encounters a diverter. Vials that are destined for locations beyond the target station are allowed to group. Vials that are behind a vial destined for the target station are held to introduce a gap between the vial destined for the target station and the remaining vials. By grouping vials according to need rather than singulating all vials, the disclosed pharmaceutical vial processing system and method reduces vial processing time and improves throughput.

BRIEF DESCRIPTION OF THE DRAWINGS

FIG. 1 is a schematic diagram of an automated dispensing line employing a diversion algorithm according to an example embodiment.

DETAILED DESCRIPTION OF EXEMPLARY EMBODIMENT(S)

Referring to FIG. 1, a schematic diagram of an automated dispensing line employing a diversion algorithm according to an example embodiment is shown. An automated dispensing line may comprise a plurality of conveyors 100 102 for transporting vials 116 118 120 to automated tablet counters (ATC), sorting stations 104 106, and other locations on the line. Vials are diverted to various locations on the line using mechanical diverting devices 108 110 112 114 that "push" a vial from one direction of travel to another. In an example embodiment, each diverter comprises an RFID reader that reads an RFID tag associated with the vial. In an example embodiment, each vial is transported in a puck that contains the vial and comprises the RFID tag for use in routing the vial on the line and dispensing a medication from an ATC into the vial.

A diversion algorithm executing in conjunction with a line control application that controls processing of prescription orders and other aspects of line functionality identifies vials that need to be diverted to a new location or to a new direction of travel on the line for further processing. When traveling in the same line of direction, vials are allowed to group (i.e., touch with no gaps) and gaps between vials are not introduced or maintained. When the diversion algorithm determines a target vial is approaching a diverter that should be engaged to divert the vial to a target station, the diversion algorithm analyzes the destinations of the vials surrounding the target vial to determine whether the vial's "neighbors" will be traveling beyond the target station. If none of the vial's neighbors are destined for stations or locations beyond the target station, the vials remain in a group while traveling on the line. The target vial, which is the last one in the group 116, remains with the group until it arrives at the target station 104. The diverter 108 verifies the RFID tag for the target vial 116, engages the "diverting" or "pushing" mechanism 108, and the target vial 116 is diverted to the target station 104. The remaining vials in the group continue in the original direction of travel.

If the diversion algorithm determines that one or more of the target vial's neighbors 120 are destined for stations or locations beyond the target station 106, the vials 120 behind the target vial 118 are held until the target vial 118 is diverted to the target station 106. The held vials 120 are then released to continue travelling down the conveyor. In an example embodiment, vials are held on the line using a hold arm 122 124 126 128 that is engaged when the diversion algorithm determines that one or more vials need to be held until a target vial is diverted to a target station.

Additional features of the line control application that increase the throughput of the dispensing line and/or reduce processing times include the following: Multi-vial Order Processing; Aged Order Processing; and Tote Sorter.

Multi-Vial Order Processing

A single order for a member may comprise one or more drugs or items that can be "auto-filled" on the automated dispensing line and one or more drugs or items that must be manually processed. The "auto-fill" process requires less time (e.g., 30-45 seconds) than a manual fill (1-3 minutes) so to increase the likelihood that the entire order is completed at approximately the same time, the manual fill portion of the order is initiated before the auto-fill process.

When the line control application reads an order, it identifies the items that require a manual fill process (e.g., by looking up each item in a database.) The order is split into items that can be auto-filled and items that are manually filled. Processing of the manual fill items is initiated before processing of the auto-fill items to increase the likelihood that processing of all items will be complete at approximately the same time. As items for a split order are processed, they are directed to an order sorter that holds the items for the entire order until all of the items have been processed and are ready to be packaged. The order sorter may comprise hundreds of slots for holding items until their mates arrive. When all of the items for the order have been processed, the items in the order sorter are released and all of the items for the order proceed to packaging.

Aged Order Processing

At times, processing of auto-fill items may be delayed because an ATC is offline for maintenance or repair. When the line control application reads an order, it identifies the items that can be "auto-filled." If an ATC for a required item is offline, the order is held for processing. If the line control application determines an ATC has remained offline for an extended period of time, it identifies the orders that are waiting for the ATC and diverts the item for manual fill processing. The order is then filled rather than held indefinitely while the ATC is repaired or replaced.

Tote Sorter

In an example embodiment, orders that are manually filled are processed using totes that can hold multiple items. Additionally, orders that comprise more than a specified number of vials (e.g., 7) may be processed using one or more totes. Totes are equipped with RFID identifiers that facilitate routing of the totes on the line to one or more stations where order items are processed and added to the tote. In some instances, an order may be so large that multiple totes are required to contain the items in the order. The order is split such that some items are assigned to a first tote and the remaining items are assigned to a second tote. To facilitate processing of multi-tote orders, the tote that is processed first (e.g., all items assigned to the tote have been picked) may be diverted to a tote sorter that holds the tote until its mate arrives. In an example embodiment, the tote sorter comprises a circular holding plate, one entry slot, and one exit slot. A tote remains on the sorter holding plate, and recirculates, until its mate arrives. As the second tote passes by the sorter, its mate is pushed from the sorter so the two totes are regrouped for packaging.

While certain embodiments of the present invention are described in detail above, the scope of the invention is not to be considered limited by such disclosure, and modifications are possible without departing from the spirit of the invention as evidenced by the following claims:

What is claimed is:

1. A computerized method for processing vials on a dispensing line comprising:
   (a) receiving at a server a first vial identifier and a first station identifier for a first vial on said dispensing line;
   (b) receiving at said server a second vial identifier and a second station identifier for a second vial on said dispensing line;
   (c) determining at said server if said second station is located on said dispensing line after said first station; and
   (d) in response to determining at said server said second station is located after said first station, initiating a hold instruction to a hold device to hold said second vial from entering said first station.

2. The computerized method of claim 1 wherein said second vial is one of a plurality of vials behind said first vial.

3. The computerized method of claim 1 further comprising initiating a release instruction to said hold device after said first vial is diverted to said first station.

4. A computerized method for processing vials on a dispensing line comprising:

(a) receiving at a server a plurality of vial identifiers, and for each vial identifier, a station identifier for vials travelling on said dispensing line to one of a plurality of stations;
(b) identifying at said server a closest station to said plurality of vials and a vial destined for said closest station;
(c) determining at said server if at least one of said plurality of vials is destined for a station after said closest station; and
(d) in response to determining at said server that at least one of said plurality of vials is destined for a station after said closest station, initiating at said server a hold instruction to a hold device to hold vials traveling behind said vial destined for said closest station.

5. The computerized method of claim 4 further comprising initiating at said server a release instruction to said hold device after said vial destined for said closest station is diverted to said closest station.

6. A computerized method for processing vials on a dispensing line comprising:
(a) receiving at a server a drug order comprising a plurality of items;
(b) identifying by said server at least one fill item in said plurality of items that requires an exception fill process;
(c) initiating by said server said exception manual fill process for said at least one manual fill item;
(d) initiating by said server an auto-fill process for said plurality of items except said at least identified item;
(e) initiating by said server a first divert instruction to divert said identified fill item requiring an exception process to an order sorter;
(f) initiating by said server a second divert instruction to divert said auto-fill items to said order sorter; and
(g) after arrival of said identified fill item and said auto-fill items at said order sorter, initiating by said server a release instruction to release said identified fill item and said auto-fill items to packaging.

7. The computerized method of claim 6 wherein (b) identifying by said server at least one identified item in said plurality of items that requires a manual fill process comprises locating said item in a database of manual fill items.

8. The computerized method of claim 6 wherein (d) initiating by said server an auto-fill process for said plurality of items except said at least one identified item comprises initiating said auto-fill process a specified period of time after initiating said exception process.

9. The computerized method of claim 6 wherein said exception process for said at least one manual fill item comprises filling said drug order using a first tote with a first RFID identifier.

10. The computerized method of claim 9 further comprising:
(h) initiating by said server a manual fill process for additional items in said drug order;
(i) initiating by said server a first instruction to process said additional items using a second tote with a second RFID identifier;
(j) initiating by said server a second instruction to divert said first tote to a tote sorter;
(k) initiating by said server a third instruction to divert said second tote to said tote sorter; and
(l) initiating by said server a fourth instruction to release said first tote from said tote sorter for packaging.

11. The computerized method of claim 10 wherein initiating by said server a fourth instruction to release said first tote from said tote sorter comprises initiating an instruction to release said first tote when said second tote passes by said tote sorter.

12. A computerized method for processing vials on a dispensing line comprising:
(a) receiving at a server a drug order identifying at least one drug to be dispensed;
(b) determining by said server a period of time an automated table counter for said at least one drug is offline; and
(c) after said period of time, initiating by said server an exception process for said order of said at least one drug.

13. The computerized method of claim 12 further comprising initiating by said server a manual fill process for additional orders of said at least one drug.

14. The computerized method of claim 13 wherein said additional orders are processed using a plurality of totes.

15. The computerized method of claim 14 further comprising initiating by said server a divert instruction to divert at least one tote for at least one additional order to a tote sorter.

16. The computerized method of claim 15 further comprising initiating by said server a release instruction to release said tote from said tote sorter when a mate for said tote passes by said tote sorter.

* * * * *